United States Patent [19]
Allum

[11] Patent Number: 5,919,149
[45] Date of Patent: Jul. 6, 1999

[54] METHOD AND APPARATUS FOR ANGULAR POSITION AND VELOCITY BASED DETERMINATION OF BODY SWAY FOR THE DIAGNOSIS AND REHABILITATION OF BALANCE AND GAIT DISORDERS

[76] Inventor: John H. Allum, Hebel Str. 109, Basel, Switzerland, CH-4056

[21] Appl. No.: 08/818,319

[22] Filed: Mar. 14, 1997

Related U.S. Application Data

[60] Provisional application No. 60/029,010, Oct. 24, 1996.

[51] Int. Cl.⁶ .................................................. A61B 5/103
[52] U.S. Cl. ............................................................. 600/595
[58] Field of Search .................................... 600/587, 595; 73/862.042, 865.4

[56] References Cited

U.S. PATENT DOCUMENTS

| | | | |
|---|---|---|---|
| 3,090,226 | 5/1963 | Corti et al. ............................... | 600/595 |
| 4,092,633 | 5/1978 | Fletcher et al. ...................... | 340/213 R |
| 4,738,269 | 4/1988 | Nashner ................................... | 128/782 |
| 4,817,633 | 4/1989 | McStravick et al. .................... | 128/782 |
| 4,830,024 | 5/1989 | Nashner et al. ......................... | 128/787 |
| 4,848,358 | 7/1989 | Nitzan et al. ............................ | 128/740 |
| 4,938,476 | 7/1990 | Brunelle et al. ......................... | 600/595 |
| 5,052,406 | 10/1991 | Nashner ................................... | 128/782 |
| 5,209,240 | 5/1993 | Jain et al. ................................ | 128/779 |
| 5,281,957 | 1/1994 | Schoolman .................................... | 345/8 |
| 5,303,715 | 4/1994 | Nashner et al. ......................... | 128/782 |
| 5,337,757 | 8/1994 | Jain et al. ................................ | 128/779 |
| 5,361,778 | 11/1994 | Seitz ........................................ | 128/779 |
| 5,368,042 | 11/1994 | O'Neil et al. ............................ | 600/595 |
| 5,469,861 | 11/1995 | Piscopo et al. .......................... | 128/781 |
| 5,551,445 | 9/1996 | Nashner ................................... | 128/782 |
| 5,627,327 | 5/1997 | Zanakis .............................. | 73/862.042 |
| 5,749,372 | 5/1998 | Allen et al. .............................. | 600/595 |

FOREIGN PATENT DOCUMENTS

| | | |
|---|---|---|
| 3416873 A1 | 11/1985 | Germany . |
| WO 88/04909 | 7/1988 | WIPO . |

OTHER PUBLICATIONS

G.H. Begbie, "Some Problems of Postural Sway", in "Myotatic, Kinesthetic and Vestibular Mechanisms", pp. 80–104 (A.V.S. deReuck & Julie Knight, eds., 1967).

L.M. Nashner, "A Model Describing Vestibular Detection of Body Sway Motion", Acta Otolaryng 72, pp. 429–436, 1971.

E.V. Gurfinkel, "Physical Foundations of the Stabilography", Agressologie, 14, C, pp. 9–14, 1973.

(List continued on next page.)

*Primary Examiner*—Max Hindenburg
*Attorney, Agent, or Firm*—Foley & Lardner

[57] ABSTRACT

A method and apparatus for the diagnosis and rehabilitation of abnormal postural sway of a subject during standing or the performance of movement tasks is provided. Body sway sensors, such as angular velocity transducers, are attached to the body, such as the upper torso, of the subject. Output signals from the body sway sensors are transformed into detailed body sway angular displacement and velocity information by a system processor. The body sway angular displacement and velocity information may be displayed to an operator for diagnosis of the subject's balance or gait disorders. The angular displacement and velocity information may also be provided as feedback to the subject, to augment the signals normally used by the subject's brain to help stabilize body sway and improve balance. Rehabilitory feedback may be in visual, auditory, and/or tactile form, and/or in the form of electrical stimulation of the vestibular nerve. For visual feedback, a lightweight imaging system mounted on a pair of eyewear may be used to project a body sway angle and angular velocity feedback display into an eye of the subject. An angular position and velocity based body sway diagnosis system in accordance with the present invention may be used to monitor simultaneously the body sway of multiple subjects, and to provide rehabilitory feedback to such subjects, without interfering with or restricting the normal movement activities of the subjects.

67 Claims, 5 Drawing Sheets

OTHER PUBLICATIONS

J. Dichgans, et al., "Postural Sway in Normals and Atactic Patients: Analysis of the Stabilizing and Destabilizing Effects of Vision", Agressologie 17, C, pp. 15–24, 1976.

L.M. Nashner, "Adapting Reflexes Controlling the Human Posture", Exp. Brain Res., vol. 26, pp. 59–72, 1976.

S.H. Koozekanani, "On the Role of Dynamic Models in Quantitative Posturography", IEEE Trans. Biomed. Eng., vol. BME–27, No. 10, pp. 605–609, Oct. 1980.

F. Owen Black, et al., "Effects of Visual and Support Surface Orientation References Upon Postural Control in Vestibular Deficient Subjects", Acta Otolaryngol 95, pp. 199–210, 1983.

Mary E. Tinetti, et al., "Fall Risk Index for Elderly Patients Based on Number of Chronic Disabilities", Am. J. Med., vol. 80, pp. 429–434, Mar. 1996.

F. Owen Black, et al., "Effects of Unilateral Loss of Vestibular Function on the Vestibulo–Ocular Reflex and Postural Control", Ann. Otol. Rhinol. Laryngol. 98, pp. 884–889, 1989.

Emily A. Keshner & John H.J. Allum, "Muscle Activation Patterns Coordinating Postural Stability from Head to Foot", in "Multiple Muscle Systems: Biomechanics and Movement Organization", pp. 481–497, (J.M. Winters & S.L.–Y. Woo, eds., 1990).

Kamran Barin, "Dynamic Posturography: Analysis of Error in Force Plate Measurement of Postural Sway", IEEE Eng. in Med. Biol., vol. 11, No. 4, pp. 52–56, Dec., 1992, D. Perennou, et al., "Optoelectronic assessment of upper body sway in erect posture: validation for 3–D stabilometry", in "Vestibular and neural front", pp. 57–60, (K. Taguchi, et al., eds., 1994).

Y. Ehara, et al., "Comparison of the performance of 3D camera systems", Gait & Posture, vol. 3, pp. 166–169, Sep. 1995.

Thomas E. Prieto, et al., "Measures of Postural Steadiness: Differences Between Healthy Young and Elderly Adults", IEEE Trans. Biomed. Eng., vol. 43, No. 9, pp. 956–966, Sep. 1996.

METHOD AND APPARATUS FOR ANGULAR POSITION AND VELOCITY BASED DETERMINATION OF BODY SWAY FOR THE DIAGNOSIS AND REHABILITATION OF BALANCE AND GAIT DISORDERS

This application claims the benefit of U.S. Provisional Application No. 60/029,010, filed Oct. 24, 1996.

FIELD OF THE INVENTION

This invention pertains generally to methods and devices for providing non-invasive testing of the postural sway of a human subject during standing or movement tasks, and more particularly to such methods and devices that employ direct measurement of body position using displacement or motion transducers or other sensing devices attached to the body. This invention also pertains generally to prosthetic methods and devices for aiding in the rehabilitation of balance and gait deficits and, more particularly, to such methods and devices that provide feedback of postural information to the subject.

BACKGROUND OF THE INVENTION

Individuals who suffer from a balance control deficit are abnormally prone to falling and have poor gait control when walking or engaging in other movement tasks. A balance control deficit may be the result of a wide variety of sensory and/or motor disorders that impair the posture and equilibrium control of the subject. In order to make a correct assessment of a subject's balance deficit, and thereby to take remedial measures, an examining physician, or physical therapist, must determine the subject's balance control ability for a number of motor tasks, such as standing, getting up out of a chair, walking down steps, etc. By observing the subject performing such motor tasks, the physician may be able to determine if the subject's balance control is within normal limits and, if not, how best to bring balance control near or within normal limits again. However, to provide a more accurate and objective assessment of the individual's sensory and motor components of posture and equilibrium, a test system which provides an objective quantifiable assessment of balance control is required.

Quantitative information on the human sense of balance can be obtained using a variety of methods and devices. Quantitative information on the efficacy of the human sense of balance can be obtained by the electrophysiological measurement of eye movements or of the postural responses of the limbs. A balance control deficit is indicated if a response is outside of the limits expected for individuals having a normal balance function. Quantitative postural information may also be obtained by measuring contractile activity of the muscles generating the internal body forces for maintaining the equilibrium position using electromyographic (EMG) recordings.

Balance deficits are, however, normally quantified by recording body sway, i.e., the displacement of the body from the equilibrium position. Quantification of the postural sway of a subject is known as "stabilometry" or "posturography". One such method for quantifying balance deficits involves the measurement of body sway in terms of displacement of the center of foot pressure (CFP), sometimes termed "center of force", generated by the inherent instability of a test subject standing on a fixed support surface. CFP is computed from the signals provided by force transducers which are typically embedded in the four corners of the support surface. The force transducer outputs are employed to obtain a projection, on the support surface platform, of the resultant forces acting at the subject's center of gravity. An anterior, front-to-back, projection is obtained by assuming that the difference between the force detected by the for and aft force transducer-pairs equals torque about the ankle joint. The anterior projection is obtained by dividing the ankle torque by the total vertical force. This calculation also assumes that the upright body can be represented by a simple upright pendulum. Thus, only the effect of movement at the ankle joints is considered, the effect of movements at the knee and hip joints is ignored. A similar calculation employs the signals provided by the lateral pairs of force transducers on each side of the support platform to obtain a lateral force projection. The vectorial sum of the anterior and lateral force projections equals the CFP. As body sway frequencies exceed 0.2 Hz, however, this method for estimating the movement of the body's center of gravity based on CFP becomes increasingly inaccurate, because oscillations of the upper body enter the CFP measurements as inertial reaction forces. Furthermore, if the multi-link nature of the body is ignored, serious errors in understanding a subject's balance disorders can occur.

Investigators have used different types of force platforms to analyze postural sway. Some such force platforms are specifically targeted towards tests for analyzing balance disorders caused by vestibular deficits. Quantitative examination of CFP data suggests that subjects having a unilateral vestibular balance deficit, e.g., a balance deficit caused solely by impairment of the vestibular end organs in the ear, perform within normal ranges when tests are employed using a fixed force sensitive support surface to perform the balance tests. For this reason, techniques have been introduced which make the control of spontaneous sway by a subject positioned on the CFP measuring support surface more difficult. These techniques make quantification of a vestibular balance deficit easier by interrupting the non-vestibular sensory inputs that the subject may otherwise use to maintain his balance. One such technique involves moving the support surface so that it is tilted (forward or backward) in relation to changes in the subject's CFP. This type of controlled platform instability may be obtained using a purely mechanical device, or with a more flexible electronic and computer controlled motor unit. The movement of the support surface platform disrupts the somatosensory inputs which would otherwise be available to the subject. A second technique involves the use of a movable visual surround, which surrounds the subject, and which is moved to follow the subject's body sway, as estimated by CFP measurement of the subject. This technique disrupts the visual stabilization inputs used by the subject to maintain balance control. By disrupting the somatosensory and visual inputs, a test procedure for analyzing a subject's balance control is able to focus more particularly on the vestibular balance control mechanism. Examples of such test systems and procedures are described in more detail in U.S. Pat. Nos. 4,738,269, 5,052,406, and 5,303,715 issued to Nashner, et al. Analysis of tests employing these improvements to CFP sway quantification have indicated that destabilization of the support surface beneath the subject provides a major diagnostic improvement. However, destabilizing a visual surround by moving it in relation to the CFP provides little additional diagnostic information as far as vestibular balance deficit is concerned.

A major drawback of CFP based systems for quantifying body sway is that the freedom of movement of the subject is limited by the fact that the subject must remain in contact with the force sensing support surface. Thus, the physician's ability to determine a subject's balance control while performing a variety of motor tasks is limited by the CFP method. A more flexible system that may be used to measure body sway employs light-weight light-emitting sources that are mounted on a subject's body. However, such three-dimensional camera based systems are typically prohibitively expensive for most physical therapy practices specializing in rehabilitation of gait and balance deficits. Moreover, these systems also have a number of technical drawbacks, including excessive computer power requirements, limited on-line capabilities, sensitivity to interfering light sources, and limited range of operation. Thus, although such systems are capable of quantifying gait and other dynamic postural abnormalities, which cannot be achieved using CFP measuring support surfaces, this advantage is outweighed by the price and ease-of-operation advantages of more conventional CFP systems. Thus, CFP systems are still the system of choice for quantifying the body sway of subjects with balance deficits.

After a balance deficit has been diagnosed and quantified, a physician may prescribe remedial measures to bring the subject's balance control near or within normal limits. The physician may prescribe medication that reduces the action of peripheral senses on the brain. Alternatively, the physician may prescribe a course of physical therapy, which will typically last at least several weeks, with the object of training the subject's brain to deal with a reduced sense of balance when trying to maintain the body upright and prevent a fall. However, neither of these techniques will have an immediate rehabilitory effect on the subject's balance deficit. Moreover, medication can have side effects, and can also reduce the capability of the brain to process balance information from the peripheral senses. A course of physical therapy requires a long training period which may extend over more than two months. These difficulties and limitations associated with conventional remedial measures for dealing with balance deficits are most problematic when the subject is older and likely to have a falling tendency.

In the field of hearing, which is physiologically related to that of balance, two types of prostheses are used to augment a subject's hearing ability. The first type of device involves augmenting the sound waves in the external ear canal so that they have greater excursions when they reach the inner ear where they are transduced into electrical signals that reach the brain. The second type of device for improving hearing ability involves direct electrical stimulation of the auditory nerve in the inner ear. For the sense of balance, however, in which sensory signals from different neurophysiological systems, including a major input from the vestibular system of the inner ear, are combined by the brain to yield a unitary sense of balance, no prosthetic device exists.

SUMMARY OF THE INVENTION

The present invention provides a method and apparatus for performing non-invasive, sensitive, and reliable tests for the presence of abnormalities in the postural sway of a human subject during standing or movement tasks. A method or device in accordance with the present invention may be used as both a diagnostic and a rehabilitation tool for subjects who are prone to abnormal falling or who wish to improve their movement control. The present invention may specifically be used to provide prosthetic feedback to aid in the rehabilitation of balance and gait deficits.

The method and apparatus of the present invention is based on the finding that the unitary sense of balance computed by the human brain involves monitoring the upper body and maintaining the angular position and angular velocity of the body within a cone of angular stability. Once this cone of stability is exceeded, with an excessive angular velocity, normal individuals will respond by correcting the trunk position within 200 milliseconds.

The present invention employs light-weight wearable body sway sensors, such as velocity transducers, that are preferably attached to the upper body, e.g., the chest, of a subject. The sensor output signals are transformed into detailed angular displacement and velocity information. The subject need not remain in contact with a support-surface in order for body sway measurements to be made, therefore, subject movement is not restricted. Moreover, the body sway sensors employed in the present invention are not limited in accuracy by the assumptions used for calculating body sway based on CFP from the signals provided by force transducers embedded in a force plate support surface.

Signals from the body sway sensors on the subject are provided to a microprocessor based system processor. The system processor is programmed to transform the angular position and velocity information provided by the sensors into useful information formats that are displayed to an operator on an operator's display unit. Quantified body sway information that may be provided to the operator as part of the operator's display includes: time histories of the subject's angular sway deviations and angular velocity in the roll and pitch directions, histograms of the sway deviations and sway velocities over an examination trial period for the roll and pitch directions, a measurement of the total vectorial angular path transversed by the subject's upper body during the examination trial period, and measures of maximum instability in the roll and pitch directions. The operator's display may also provide for comparisons between examination trial results from different trials or between examination trial results and body sway information obtained from a normal sample population. Moreover, the operator's display may provide an objective measure of the subject's stability by comparison of the subject's zero-velocity cone of stability with the maximum trunk sway angle deviations occurring during the examination trial period. Since the body sway sensors employed by the present invention do not interfere with subject movement, this detailed information may be obtained for examination trials involving the performance of a wide variety of movement tasks by the subject.

The system processor of the present invention may also be programmed to provide rehabilitory postural feedback to the subject based upon the body sway angle and sway velocity information obtained from the body sway sensors. This feedback may be in the form of visual, auditory, or tactile stimulation, or may be provided in the form of an electrical signal that is used to directly stimulate the vestibular nerve. A single type of feedback may be used, or different types of feedback may be provided to a subject in combination. The rehabilitory feedback immediately augments the balance signals normally used by the subject's brain to help stabilize body sway and improve balance. The feedback gain, the amount of feedback provided to the subject relative to the measured body sway angle and angular velocity, may be adjusted by the system operator. The information provided on the operator's display provides an objective measure for determining improvements in balance brought about by the application of feedback, and by altering feedback gains.

For visual feedback, a visual feedback system incorporated in a pair of lightweight eyewear may be used. An imaging system mounted in the eyewear is used to project a visual feedback display generated by the system processor into the eye of the wearer of the eyewear. Because the viewer's vision is not otherwise restricted by the eyewear, the projected display appears to float in the normal visual field of the subject. The subject is thus able to see both the world around him and the display simultaneously. The visual feedback display preferably includes a horizontal bar that moves in relation to the forward and backward (pitch) and left and right (roll) sway of the subject's upper body. The width of the horizontal bar increases or decreases in relation to the vectorial combination of the roll and pitch velocities of the subject's upper body. As the subject's angular sway approaches the subject's angular cone of stability, a portion of the horizontal bar flashes to indicate to the subject that he is in danger of falling. The sensitivity of the movement and width of the horizontal bar to the sway angle and sway velocity of the subject, as well as the proximity of the subject's sway to the cone of stability necessary for a warning to be indicated, are visual feedback gain parameters, which may be adjusted by the operator to help improve the subject's control of body sway, and therefore improve the subject's balance control for selected movement tasks.

For auditory feedback, the information which is visually displayed when used for visual feedback is presented to the subject aurally. Roll and pitch angular displacements of the subject may be provided as frequency modulations around two different audible tone center frequencies, e.g., 500 Hz and 1500 Hz. The velocity of angular sway may be presented as an increased or decreased tone volume. A warning that the subject is approaching his cone of stability can be given in the form of an audible warning signal that is provided to the subject. The depth of frequency modulation, loudness of the auditory signals, and conditions for providing the warning signal, are auditory feedback gain parameters which may be set by the operator to help improve the subject's control of body sway, and therefore improve the subject's balance control for one or more movement tasks.

Tactile feedback may be provided by vibrators that are used to convey a sense of rotation of the subject's torso. For example, two vibrators placed on the subject may be used to convey a sense of forward and backward sway by modulation of the frequency of vibration with respect to the measured sway velocity, and by varying the amplitude of vibration with respect to the sway angle. A separate vibrator may be used to signal the subject that the sway angle has exceeded the limits of safety for the subject. Each of these parameters, modulation frequency, amplitude of vibration, and the body sway safety limit, is a tactile feedback gain parameter that may be adjusted by an operator to improve the subject's control of body sway and therefore improve the subject's balance control for one or more movement tasks.

Body sway and sway velocity feedback signals may also be provided as varying electrical signals which are used to directly stimulate the vestibular nerve. Such stimulation is sensed by the subject as a change in the angular and/or linear position of the head. Feedback signals for such direct electrical stimulation are transmitted transcutaneously to an implantable device directly connected via electrodes to the close proximity of the vestibular nerve or to the nerve itself. The pulse rate, amplitude, and duty cycle of the electrical stimulation signal at the electrodes is varied with respect to the sway angle and angular velocities that are determined by the system processor based on the signals provided by the body sway sensors attached to the subject's upper body. The relationship of the signal amplitude, pulse rate, and duty cycle to the body sway angles and angular velocity are among the adjustable feedback gain parameters for this type of feedback.

Besides providing a more accurate and reliable method and apparatus for testing for the presence of balance disorders, and for providing rehabilitation feedback to improve such disorders, the present invention may also be used to monitor the safety of a large number of subjects who are in danger of falling, as well as for providing a record of how and when a subject, for example, in a home for the elderly, actually fell. In accordance with the present invention, a subject's body sway angle and sway angular velocity is measured using light-weight wearable body sway sensors that don't restrict the subject's movement. Thus, continuous subject monitoring may be obtained, and feedback provided, without significantly interfering with the subject's day-to-day activities. The information provided by the wearable body sway sensors may be continuously provided to a system processor attached to the subject and stored therein for future analysis. Moreover, the body sway signals provided by the body sway sensors worn by multiple subjects may be provided, via conventional wireless transmission techniques, to a "remote" system processor, whereby the safety of a large number of subjects may be monitored simultaneously. Such a system may be programmed to provide warnings to the operator when one of the subjects exceeds a pre-defined body sway safety limit for that subject, indicating that the subject is in danger of falling.

DETAILED DESCRIPTION OF THE INVENTION

Figure 1:
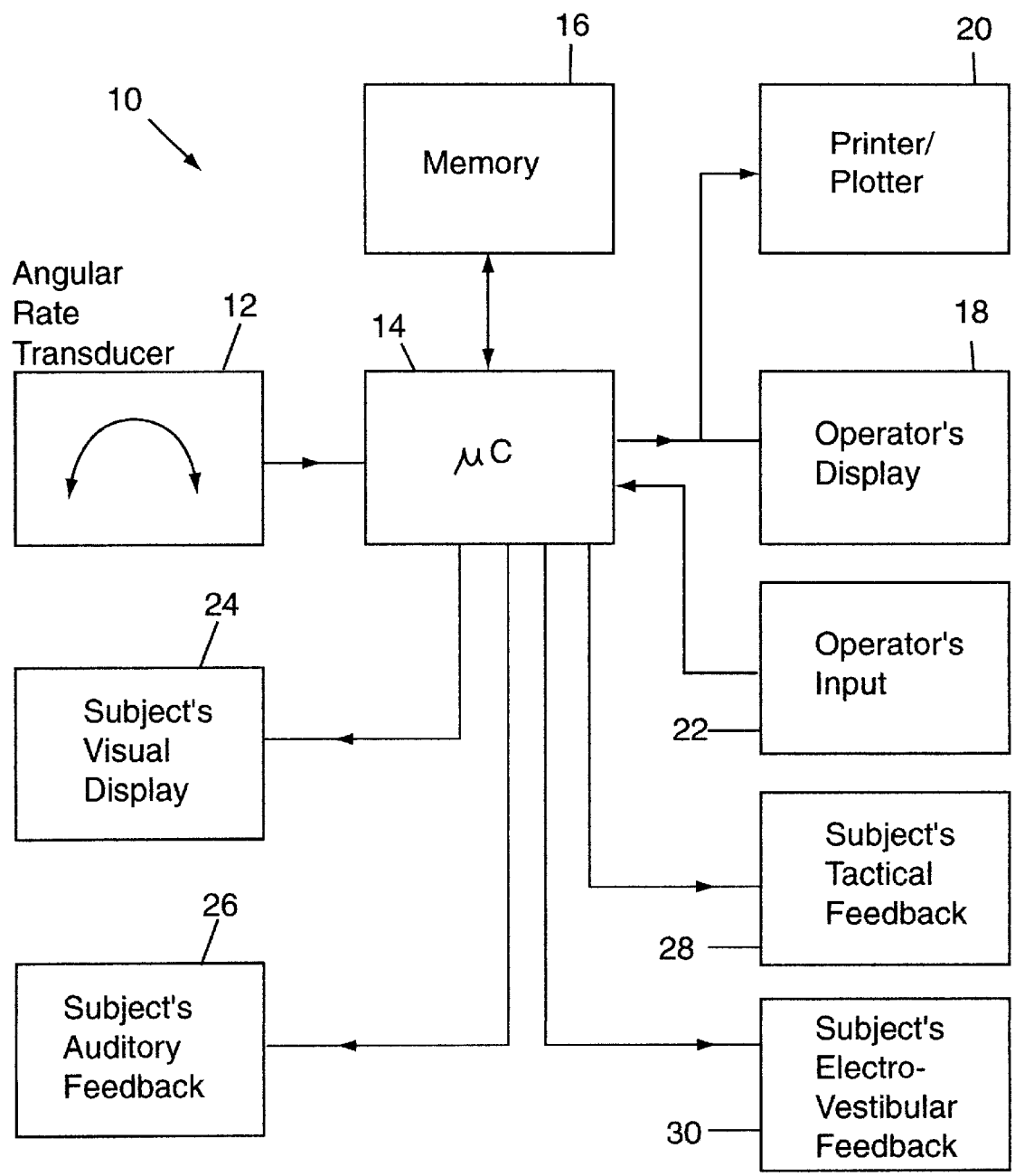
FIG. 1 is a schematic block diagram of an angular position and velocity based body sway diagnosis and rehabilitation system in accordance with the present invention.

The present invention provides a method and apparatus for significantly improving the specificity, accuracy and reliability of non-invasive diagnostic tests for the presence of balance and gait disorders. The present invention also provides a rehabilitory method and apparatus for improving a subject's balance and gait control. An angular position and velocity based body sway diagnostic and rehabilitory system for monitoring body sway and for providing body sway feedback to a subject to help improve the subject's control of body sway is illustrated generally at 10 in FIG. 1. Light-weight wearable body sway sensors 12 are attached to the upper body of a subject and provide body sway signals to a system processor 14 which derives body sway angle and body sway angular velocity information therefrom. As will be discussed in more detail below, various types of body sway sensors, including angular velocity transducers, may be used to provide body sway signals indicative of the upper body motion of a subject to the system processor 14.

The system processor 14 may be implemented as a conventional microprocessor based computer system having computer memory 16, an operator's display unit 18, e.g., a standard 14-inch computer display console, a printer or plotter 20, and an operator's input device 22, such as a conventional computer keyboard. The processor memory 16 may include short-term memory, e.g., RAM, as well as long-term memory, such as is provided by a conventional magnetic disk storage system. The system processor's memory 16 operates in a conventional manner to store the programmed series of instructions and algorithms that control operation of the system processor 14 and to store data generated by the system processor.

In accordance with the present invention, the system processor 14 is programmed to transform the body sway signals provided by the body sway sensors 12 into useful body sway angle and body sway angular velocity information formats. The body sway angle and body sway angular velocity information is displayed by the system processor 14 in the form of an operator's display that is presented to the operator on the operator's display unit 18. From this formatted information, the system operator, e.g., a physician, is able to analyze the body sway of a subject during the performance of various motor tasks, to thereby diagnose the existence of a balance or gait deficit. A hard copy of the body sway information provided on the operator's display unit 18 may be obtained using the system printer or plotter 20. It should be noted that body sway sensors 12 may also be attached to other portions of the subject's body, such as the waist, upper leg, or lower leg, to provide information on the motion of these body segments to the system processor 14, in addition to the information provided concerning the motion of the subject's trunk. The system processor 14 may be programmed to take advantage of this additional body motion information. In such a case, the system processor 14 is programmed as a motion analysis system, whose analysis results can be provided to a system operator on the operator's display unit 18. The system processor 14 may also be programmed to infer trunk angular positions and velocities from the information provided by these sensors at other, non-trunk, body locations.

In accordance with the present invention, the system processor 14 may also be programmed to provide feedback of body sway angle and angular velocity information to a subject. As will be discussed in more detail below, body sway angle and angular velocity feedback may be provided to a subject in visual, auditory, or tactile form, or may be provided in the form of a varying electrical signal for directly stimulating the vestibular nerve. Visual 24, auditory 26, tactile 28, and electro-vestibular 30 feedback systems may, therefore, be provided in accordance with the present invention to deliver body sway angle and angular velocity feedback signals provided by the system processor 14 to the subject. It should be understood that a single type of feedback, i.e., visual, auditory, tactile, or electro-vestibular, or a combination of feedback types may be provided to a subject at any one time. Thus, an angular position and velocity based body sway diagnostic and rehabilitory system 10 in accordance with the present invention need not include every feedback system 24, 26, 28, and 30 illustrated in FIG. 1, but may include any one of the feedback systems, or any combination of multiple feedback systems.

It should be noted that the functions performed by the system processor 14 may be divided among several microprocessor based systems at different locations, and in communication with each other, either through direct physical connection, e.g., using an RS-458 serial line interface, or by wireless data transmission. For example, a system processor attached to the subject's body may be programmed to provide the body sway angle and angular velocity feedback signals to a feedback system, 24, 26, 28 or 30, which is also attached to the subject's body. Simultaneously, body sway angle and body sway angular velocity information from the body sway sensors 12 may be provided, using a wireless interface, to a "remote" system processor that is not connected to the subject's body, but which is programmed to provide the body sway angle and body sway angular velocity information in the desired information format to an operator's display unit 18. This "remote" processor may be programmed to receive body sway angle and body sway angular velocity information from multiple subjects. Such a system in accordance with the present invention may be used to monitor the safety of a large number of subjects who are in danger of falling, as well as to provide a record of how and when a subject, e.g., in a home for the elderly, actually fell.

Figure 2:
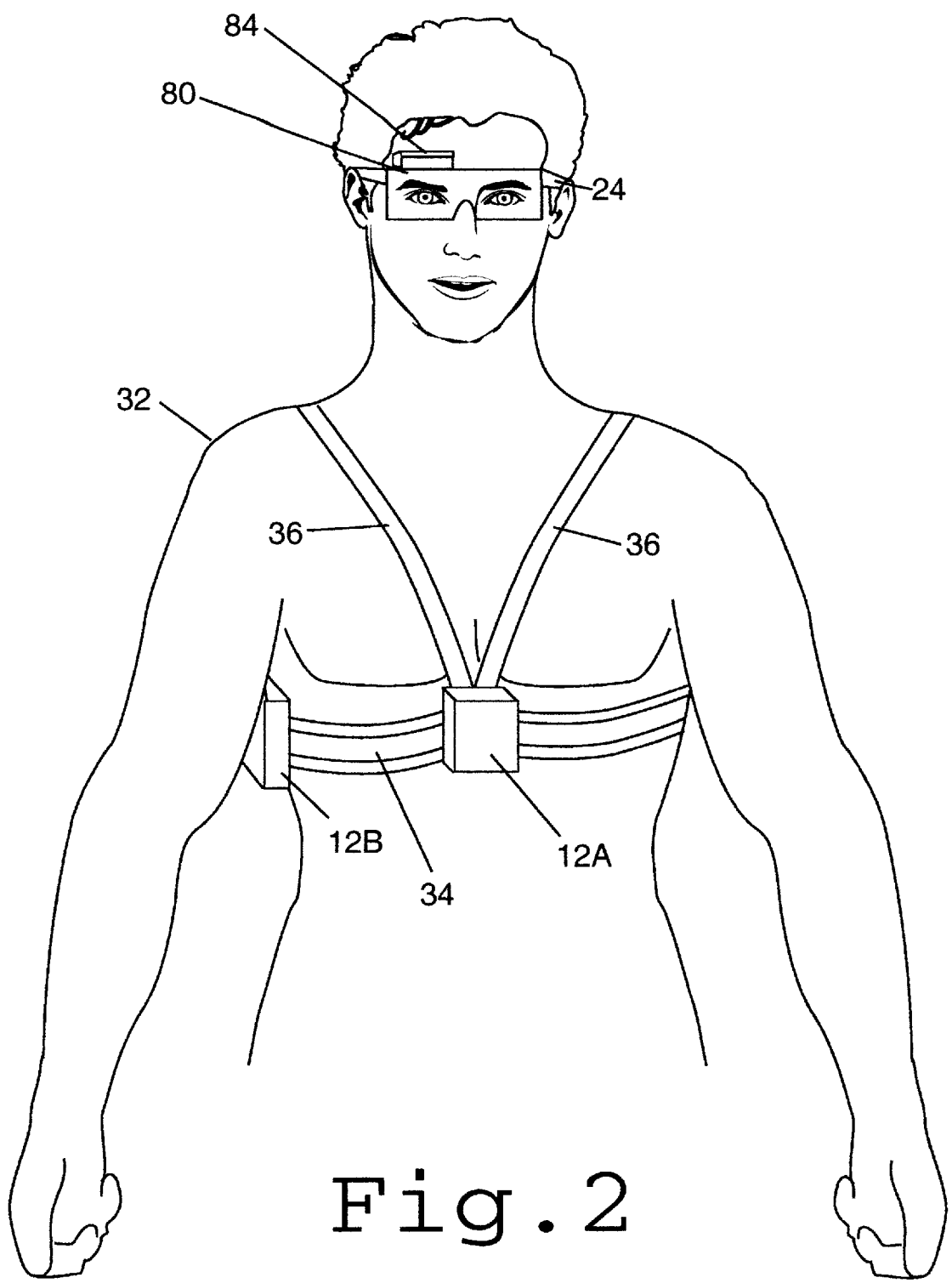
FIG. 2 is a schematic illustration of a human subject wearing body sway sensors that are used to provide body sway and angular velocity data in roll and pitch directions, and an exemplary visual body sway angle and angular velocity feedback device used for providing improved balance control in accordance with the present invention.

The location of the body sway sensors 12 on the subject's body is determined by the axis of sensitivity of the sensors. The body sway sensors 12 are preferably attached to the chest of a subject 32 to thereby register at least the roll (side-to-side) and pitch (forward and backward) motion of the subject's upper body. Preferable locations for the body sway sensors are illustrated in FIG. 2. A first sensor 12A is mounted on the front or back of the subject's chest so as to register roll, i.e., side-to-side, angular deviations of the trunk from vertical, and roll angular velocities. A second sensor 12B is mounted on the side of the subject's chest so as to register pitch, i.e., backward and forward, angular deviations from the vertical, and pitch angular velocities. The sensors 12A and 12B may preferably be secured to the chest of the subject 32 by placing the sensors 12A and 12B in tight fitting pouches attached to elasticated straps 34 which, together with support straps 36, hold the sensors 12A and 12B tightly against the subject's chest. It should be apparent, however, that other conventional means may also be used to attach the sensors 12A and 12B to the subject, either over or under the subject's clothing.

If desired, other sensors, not shown, may also be attached to the subject's chest. For example, a third sensor may be used, if desired, to register yaw, i.e., turning about the vertical axis, angular deviations, and yaw angular velocities. Similarly, the subject 32 may wear additional sensors at other bodily locations, such as at the waist, upper leg, or lower leg. These additional sensors may be used to provide information on the roll and pitch amplitudes and velocities at these body locations, in addition to the body sway angle and angular velocities of the subject's trunk. If such additional sensors are used, the present invention may be employed as a complete body motion analysis system. The system processor 14 may be programmed to analyze and display all available body motion information. Moreover, the body motion information provided by the sensors at body locations other than the trunk can be used by the system processor 14 to infer trunk sway angles and angular velocities.

Various different types of sensors 12 may be used to measure the body sway angle and body sway angular velocity of the subject 32. Preferably, the type of sensor that is used is capable of providing a direct measurement of angular velocity, i.e., an angular velocity sensor, and is substantially insensitive to the gravity vector and to linear accelerations, i.e., straight up and down, backward and forward, and side-to-side motions of the subject's entire body. An exemplary and preferred body sway sensor is the Litef Micro Fors 36 Fiber Optic Rate Sensor, made by Litef GmbH of Freiburg, Germany, D-79007. This preferred sensor is an angular velocity sensor that may be programmed to provide either angular deviation or angular velocity information in digital form, at a selected scale factor, to the system processor 14 which stores and transforms the digital angular deviation or velocity values into an information format which is provided to the system operator. For this angular velocity sensor, the angular velocity scale factor is relative to a maximum sensed rate of 327 degrees per second.

Body sway sensors which measure Coriolis forces in vibrating structures to sense angular velocities may also be used. Such a sensor is, for example, available as part number ADS-C232 from Watson Industries, Inc. of Eau Claire, Wis., U.S.A. This exemplary product has a scale factor of 30 degrees per second per volt. Similar products are also available. This type of sensor is, however, not preferred, because such sensors generally provide an analog output, requiring the use of an analog-to-digital converter, to be placed between the sensor 12 and the digital system processor 14, in order for the sensor signals to be processed digitally by the system processor 14. Acceptable forms of this type of sensor device may, however, become available in the future. An acceptable device would, for example, be a miniaturized version of the system produced by Watson Industries, or its equivalent, with the capability of providing direct digital outputs over a serial line interface to a computer, such as the system processor 14.

The body sway sensors 12 may also be implemented using pairs of linear acceleration transducers (accelerometers) set at fixed distances from one another on a subject's body. Such devices may be used to measure angular accelerations, which may then be transformed into angular velocity and angular deviation values by suitable analog or digital integration algorithms implemented, for example, in the system processor 14. However, it is noted that most linear accelerometers have inherent drift problems. Thus, the use of linear accelerometers to provide body sway sensing is not preferred, unless the drift problems currently inherent in most linear accelerometers are reduced.

Whatever type of body sway sensors 12 are used, it should be clear that it is not crucial that the inputs to the system processor 14 be angular velocity signals, although this is preferred. If angular displacement signals are provided to the processor 14, these must be differentiated to obtain angular velocity. If angular acceleration signals are provided by the sensors 12, these must be integrated by the system processor 14 to obtain angular velocity and displacement. Standard digital differentiation and integration algorithms may be used by the system processor 14 to perform the differentiation and integration functions, as necessary.

Figure 3:
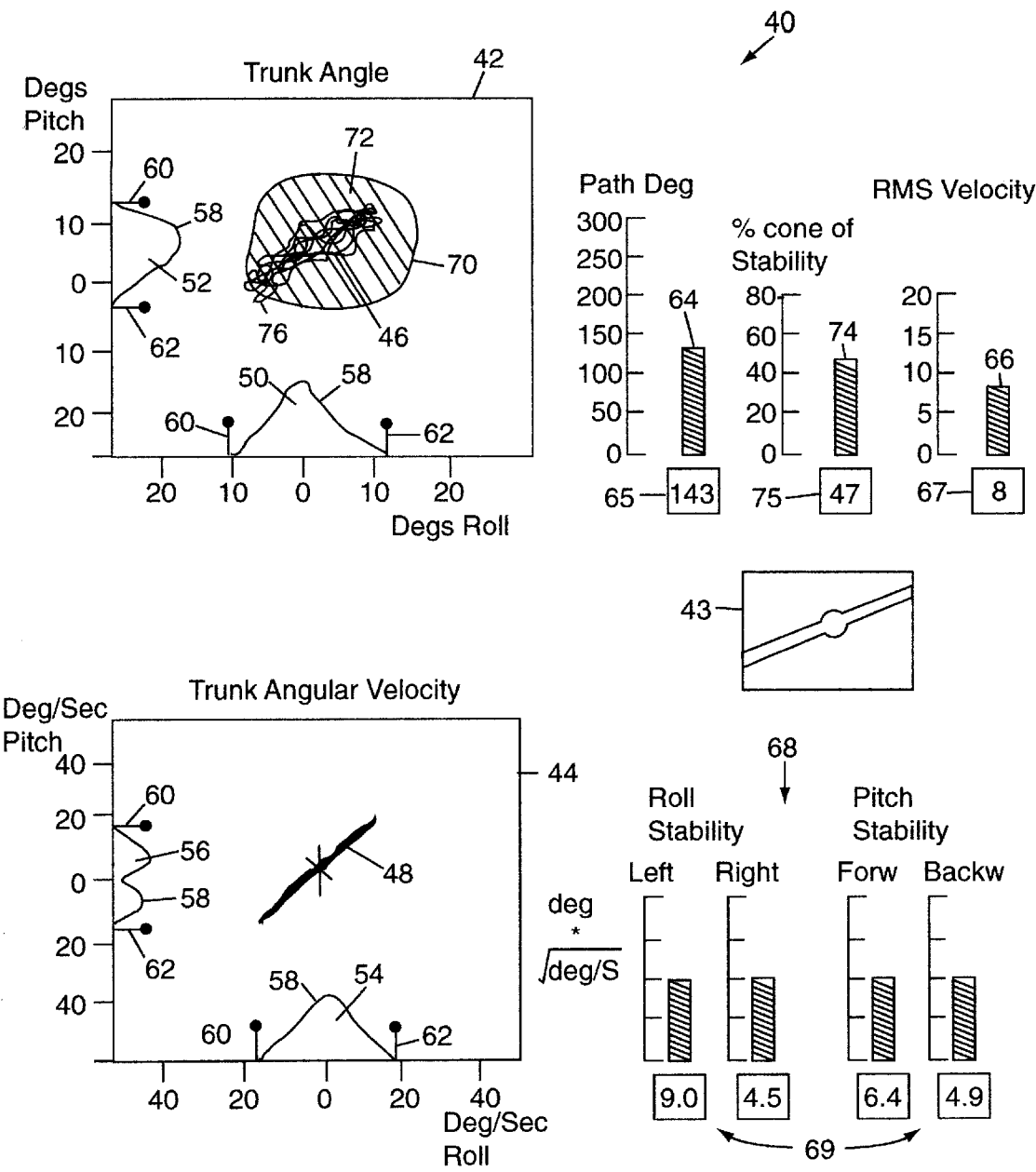
FIG. 3 is an illustration of an exemplary operator's display for providing body sway angle and angular velocity information to an operator in accordance with the present invention.

Transformed sensor signal information quantifying body sway angle and body sway angular velocity may be displayed in a number of useful formats to an operator in the form of an operator's display provided on the operator's display device 18. An exemplary preferred format for providing to the operator a display of a measured subject's (the wearer's) trunk angular displacement and trunk angular velocity is illustrated in FIG. 3. The preferred operator display 40 includes insert displays 42, 43, and 44 for displaying trunk angular displacement and trunk angular velocity information in various formats. Insert display 43 is identical to the subject's visual feedback display which is illustrated in and which will be described in more detail below with reference to FIG. 5, but may be reduced in size. The other insert displays 42 and 44 display trunk angle and trunk angular velocity information, respectively, in various formats.

A time history of the subject's angular sway deviations 46 and angular sway velocity 48 in the roll and pitch directions, over a selected examination trial period, is provided in the center of the insert displays 42 and 44, respectively. The displacement in a horizontal direction of an individual point in the time history displays 46 and 48 from the center of the insert displays 42 and 44 represents degrees of roll or degrees per second of roll, respectively. Degrees of pitch and degrees per second of pitch are represented by displacements in the vertical direction from the center of the trunk angle insert display 42 and trunk angular velocity insert display 44, respectively.

The trunk angle insert display 42 also preferably includes histograms of the body sway angle in the roll 50 and pitch 52 directions. Similarly, the trunk angular velocity insert display 44 preferably includes histograms of the trunk angular velocity in the roll 54 and pitch 56 directions. The histograms 50, 52, 54, and 56 are displayed at the end of an examination trial period, with the respective amplitude or velocity envelope 58 and maximum values of roll and pitch angle and angular velocity in each direction indicated 60 and 62. The angular velocity envelope 58 in the roll and pitch directions can be transformed into frequency information using standard Fourier transform techniques. This frequency information may be displayed along with or instead of the angular velocity histograms 54 and 56. A bar graph 64 on the operator display 40 preferably indicates the total vectorial angular path transversed by the subject's upper body during the time of the examination trial. Another bar graph 66 on the operator display 40 preferably provides the root mean square (RMS) of the vectorial angular velocity of the subject's upper body over the time of the examination trial. Bar graphs 68 on the operator display 40 also preferably provide an indication of the maximum instability of the subject in the roll and pitch directions. Maximum instability is defined, in this case, as the maximum value of angular displacement in a particular roll or pitch direction times the square root of the maximum angular velocity in that direction. The information provided in the bar graphs 64, 66, and 68 may also be displayed numerically in numerical insert display 65, 67 and 69, respectively. Each piece of information provided on the operator display 40 is preferably updated at a rate of at least four times per second during the examination trial, which may typically last 10–30 seconds.

At the end of an examination trial, the different types of information that are provided on the operator display 40 may be compared by the operator with previous values obtained from similar tests performed on the particular subject involved in the current test, or with such values which represent a normal population. These previous subject values and normal population values may be stored in the memory 16 of the system processor 14.

The operator display 40 preferably also provides an objective measure of the subject's balance control based upon the maximum trunk angle deviations in the time history of trunk angle deviations 46 and the subject's cone of stability. It has been found that the unitary sense of balance provided by the human brain is directed toward maintaining the upper body within a maximum angular velocity within a cone of angular stability. The term "cone of stability" may be defined as the maximum leaning position of the upper body, i.e, the trunk, that a subject can achieve standing for two seconds, without falling, while attempting to keep his body as straight as possible. A normal cone of stability is that average set of values achieved by a group of at least twelve normal healthy subjects older than sixteen years of age, but below the age of 30 years. The cone of stability may be, for example, defined in eight radial directions extending from the axis of the subject's upper body (i.e., forward, forward left, left, backward left, backward, backward right, right, and forward right). The cone of stability may, of course, be defined in finer increments, such that, for example, the cone of stability is defined essentially continuously in the radial directions extending from the axis of the subject's body. The cone of stability is defined initially for near zero sway velocity, e.g., sway velocities of less than one degree per second of angular movement of the torso. The cone of stability is reduced or increased for sway velocities directed toward or away from the upright, respectively. The cone of stability defined for near zero sway velocity may preferably be reduced or increased at a rate of 1 degree per third power of sway velocity when the angular sway velocity in a particular direction exceeds 5 degrees per second.

The subject's zero velocity cone of stability 70 may be displayed in the trunk angle insert display 42. The extent of the area 72 between the cone of stability 70 and the maximum trunk sway deviations represented by the time history of the subject's angular sway deviations 46 may be shown to the operator as a bar graph 74 representing the percentage of the cone of stability 70 which is unoccupied by the area defined by the maximum trunk angle deviations. This bar graph information may also be displayed numerically in a numerical insert display 75. If some of the subject's trunk angle deviations lie outside of the cone of stability 70, e.g., area 76 in FIG. 3, this area outside of the cone of stability 70 is doubled and subtracted from the area 72 between the cone of stability 70 and the maximum trunk angle deviations in calculating the value to be displayed in the bar graph 74 and insert display 75. The value indicated in the bar graph 74 and the insert display 75, i.e., the extent of the area 72 compared to the total area within the cone of stability 70, expressed as a percentage, is a measure of the subject's stability, and provides an objective measure for determining changes in the subject's balance over time, or changes in the subject's balance brought about by altering the gain of body sway angle and angular velocity feedback signals which are provided to the subject.

It should be noted that the same information display formats that are used to provide trunk sway angle and trunk sway angular velocity information to the operator may also be used to display angular displacement and/or velocity information related to other body segments, if the appropriate sensor systems are mounted on those body segments to provide angular displacement and/or velocity information to the system processor 14. The ability to provide information displays of the angular displacement and/or angular velocity of multiple body segments makes possible the use of the angular position and velocity based body sway diagnostic system 10 of the present invention as a complete body motion analysis system.

As described previously, the present invention may be used not only for diagnostic purposes, but also to provide rehabilitation of balance and gait deficits by the provision of body sway angle and angular velocity feedback to a subject. Such feedback may be in visual, auditory, or tactile form, or in the form of direct electrical stimulation of the vestibular nerve, or a combination of such feedback types. Feedback may be provided to a subject on a continuous basis.

Figure 4:
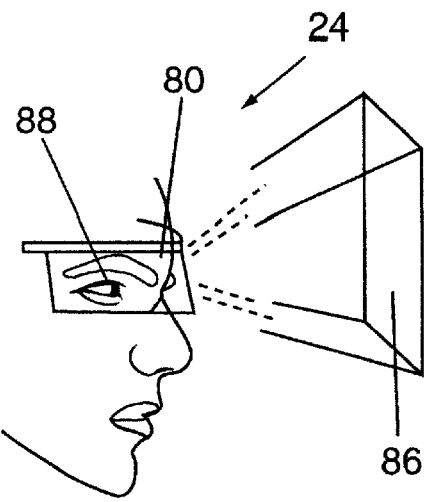
FIG. 4 is an illustration of an exemplary visual body sway angle and angular velocity feedback system in accordance with the present invention.

A system 24 for providing visual body sway angle and angular velocity feedback is described with reference to FIGS. 2 and 4. The visual feedback system 24 includes a pair of eyewear 80 which are worn by the subject 32. The eyewear 80 are preferably 60% or less light blocking. An image is projected into the subject's eye 88 by a monocular virtual imaging system 84 which may be mounted on the pair of eyewear 80. The imaging system 84 is preferably capable of projecting, at least, a standard VGA 640×480 pixel image that may be either monochrome or in color. A preferred imaging system 84 that may be used is the model Mark I or Mark II monochrome imaging system, or model Mark III color imaging system, manufactured by Seattle Site Sys. Inc. of Redmond, Wash., U.S.A. It should be noted that other image projection systems for projecting images into a subject's eyes, including a computer display image projection system which provides a binocular, stereoscopic image, might also be used to provide visual feedback in accordance with the present invention. By appropriate focusing of the image, by altering the distance between the LCD display and the lens in the imaging system 84, the image may be made to appear to the subject 32 as a large image 86, e.g., 1.5 meters across, floating in front of the subject at a distance, e.g., of 3 meters. The subject is able to view both the world around him and the image simultaneously through the eyewear 80. Although the image is illustrated in FIGS. 2 and 4 as being projected into the right eye 88 of the subject 32, the projection system 84 might also be used to project the image into the left eye of the subject 32. Preferably, the image projection system 84 is mounted on the eyewear 80 so as to project the image such that the image is viewed by the subject's dominant eye.

Figure 5:
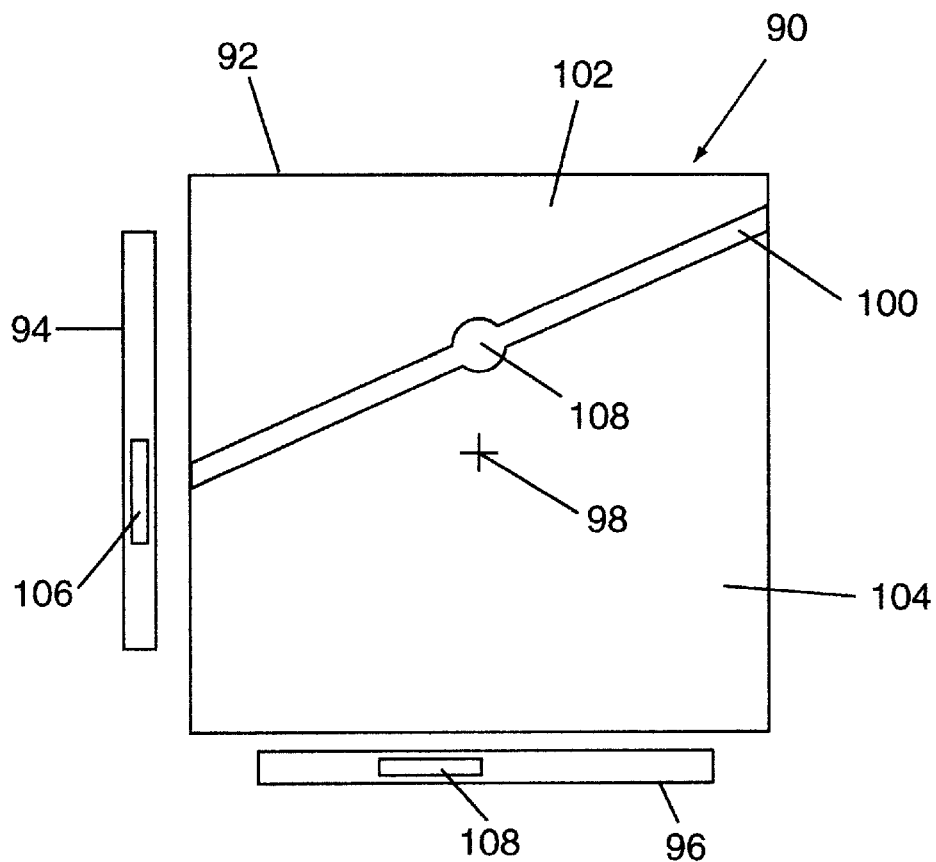
FIG. 5 is an illustration of an exemplary visual body sway angle and angular velocity feedback display in accordance with the present invention.

The image projected into the subject's eye 88 provides visual feedback to the subject of his body sway angle and angular velocity. The subject may use this information to augment the balance signals normally used by his brain to correct his body sway instabilities. A preferred format for providing visual feedback of the subject's body sway angle and angular velocity is illustrated in FIG. 5. A visual feedback display 90 includes a central frame display 92 and boundary frame displays 94 and 96. The information contained in the central frame 92 and boundary frame 94 and 96 displays relates to sway deviations from a point of reference 98. The preferred point of reference 98 is a standing point of reference which is reset by either the subject or the system operator when the subject is standing quietly with a sway velocity of less than one degree per second in both roll and pitch directions.

The central frame display 92 includes a substantially horizontally oriented bar 100 that divides the central frame display 92 into top and bottom fields 102 and 104. The top field 102 is preferably colored or shaded more lightly than the bottom field 104, with the bar 100 colored or shaded at an intermediate intensity level. The horizontal bar 100 moves upward in the central frame 92 when the subject's upper body sways forward, and moves downward, toward the bottom of the central frame 92, when the subject's upper body sways backward. Thus, the area of the dark colored field 104 increases and the area of the light colored field 102 decreases with forward sway, and the area of the dark colored field 104 decreases, and the area of the light colored field 102 increases with backward sway. The angle of the bar 100 within the central frame 92 represents roll to the left or right of the subject's upper body. A forward pitch and leftward roll of the subject's torso is thus illustrated in FIG. 5. Bar graphs 106 and 108 in the boundary frames 94 and 96 indicate the exact amounts of pitch and roll, respectively. The width of the bar 100 in the central frame 92 increases or decreases in relation to the vectorial combination of roll and pitch velocities of the subject's upper body. As the vectorial combination of roll and pitch velocities increase in a direction toward the subject's cone of stability, the width of the intermediate intensity colored bar 100 increases, thereby reducing the area of the light and dark colored fields 102 and 104. As the subject's angular sway approaches a deviation angle equal to a significant fraction, e.g., 90%, of the angular cone of stability, an enlarged center portion 108 of the bar 100 flashes, e.g., at a rate of 5 flashes per second, to indicate to the subject that he is in danger of falling. The sensitivity of the movements of the central bar 100 with respect to angular sway deviations, the sensitivity of the width of the central bar 100 with respect to the angular velocity of the subject's upper body, as well as the proximity to the cone of stability which the subject's upper body deviation angle must approach before the center 108 of the bar 100 flashes a warning, are preferably all variable parameters. These variable parameters represent the visual feedback gain of the system. The visual feedback gain parameters may be set by the operator to help improve the subject's control of sway, and therefore improve the subject's balance control for one or more movement tasks. The visual feedback gain parameters may be fine tuned by repeated movement task examination trials employing the diagnostic information features provided in the operator display 40.

The body sway information that is visually displayed to the subject by the visual feedback system 24 can, after suitable transformation, be presented to the subject aurally, using conventional audio headphones, an aural probe for insertion in the external ear canal of the subject's ear, or the like. In a preferred embodiment of an auditory feedback system 26, pitch angular displacements of the subject's upper body are presented as a tone formed by frequency modulations around a first center frequency of, e.g., 1500 Hz, and roll angular displacements are presented as a tone formed by frequency modulations around a second center frequency of, e.g., 500 Hz. Increased velocity of angular sway may be presented as an increase in the volume of the audible tones, ranging from the subject's hearing threshold at the first and second center frequencies to, for example, 20 dB less than the subject's maximum comfortable level at these frequencies. A warning that the subject's upper body is approaching the cone of stability may be given in the form of an audible word, e.g., "careful", or similar words, or another appropriate audible warning signal. For the auditory feedback system 26, the depth of frequency modulation and the volume of the audio signals with respect to the body sway angle and angular velocity, as well as the proximity to the cone of stability which the subject's upper body must approach before the auditory warning signal is given, are preferably variable parameters of the auditory feedback gain. The feedback gain parameters may be set by the operator to help improve the subject's control of sway, and therefore improve the subject's balance control for one or more movement tasks.

For tactile feedback 28, vibrators may be used to provide body sway angle and angular velocity feedback to the subject. Two vibrators, each placed in a different position on the body, and operating at, e.g., 250 Hz, may be used to provide body sway angle and angular velocity feedback for one of the pitch or roll directions. For example, a sense of forward and backward sway may be conveyed by modulation of the frequency of vibration of the vibrators in relation to the angular velocity of sway. The amplitude of the vibration corresponds to the angle of sway deviation. A similar pair of vibrators may be used to convey a sense of sway in the roll direction. An additional vibrator may be used to provide a warning that body sway is approaching or has exceeded the limits of safety, i.e., the subject's angular sway has approached within a certain percentage of the angular cone of stability. For the tactile feedback system 28, the depth of frequency modulation of the vibrators and the amplitude of the vibration with respect to the body sway angle and angular velocity, as well as the proximity to the cone of stability which the subject's upper body must approach before the warning vibrator is activated, are preferably variable parameters of the tactile feedback gain. These feedback gain parameters may be set by the operator to help improve the subject's control of sway, and therefore improve the subject's balance control for one or more movement tasks.

Body sway angle and angular velocity feedback may also be provided in the form of varying electrical signals that are used to directly stimulate the vestibular nerve. Such signals are sensed by the subject as a change in the angular and/or linear position of the subject's head. Feedback signals for direct electrical stimulation of the vestibular nerve 30 may be transmitted transcutaneously to an implantable device directly connected via electrodes to the close proximity of the vestibular nerve, or to the nerve itself. The pulse rate, amplitude, and duty cycle of the electrical stimulation provided at the electrodes may be varied according to the body sway angle and body sway angular velocities as determined by the system processor 14. As with the visual, auditory, and tactical feedback systems, the feedback gains of the system 30 for providing direct electrical stimulation of the vestibular nerve are preferably variable parameters that may be set by the operator to help improve the subject's control of sway, and therefore improve the subject's balance control for one or more movement tasks.

The feedback systems described herein may also be used to provide feedback of angular deviations and/or angular velocities of parts of the subject's body other than the trunk. This requires, however, that body motion sensors be provided at the appropriate other locations on the subject's body.

The number of times that a feedback system issues a warning signal to the subject that his upper body is approaching his cone of stability may be saved in the processor system memory 16, along with the circumstances involved (e.g., time of day, preceding pitch and roll velocities, etc.). This recorded data may be retrieved by an operator or transmitted, via wireless communications, to a central monitoring station. Further, a fall warning may be issued at this monitoring station to inform an attendant that he should investigate the possible fall of a subject prone to fall, and to take remedial action. The monitoring station may also be provided with information regarding the functional status of a particular subject's body sway angle and angular velocity feedback system.

Figure 6:
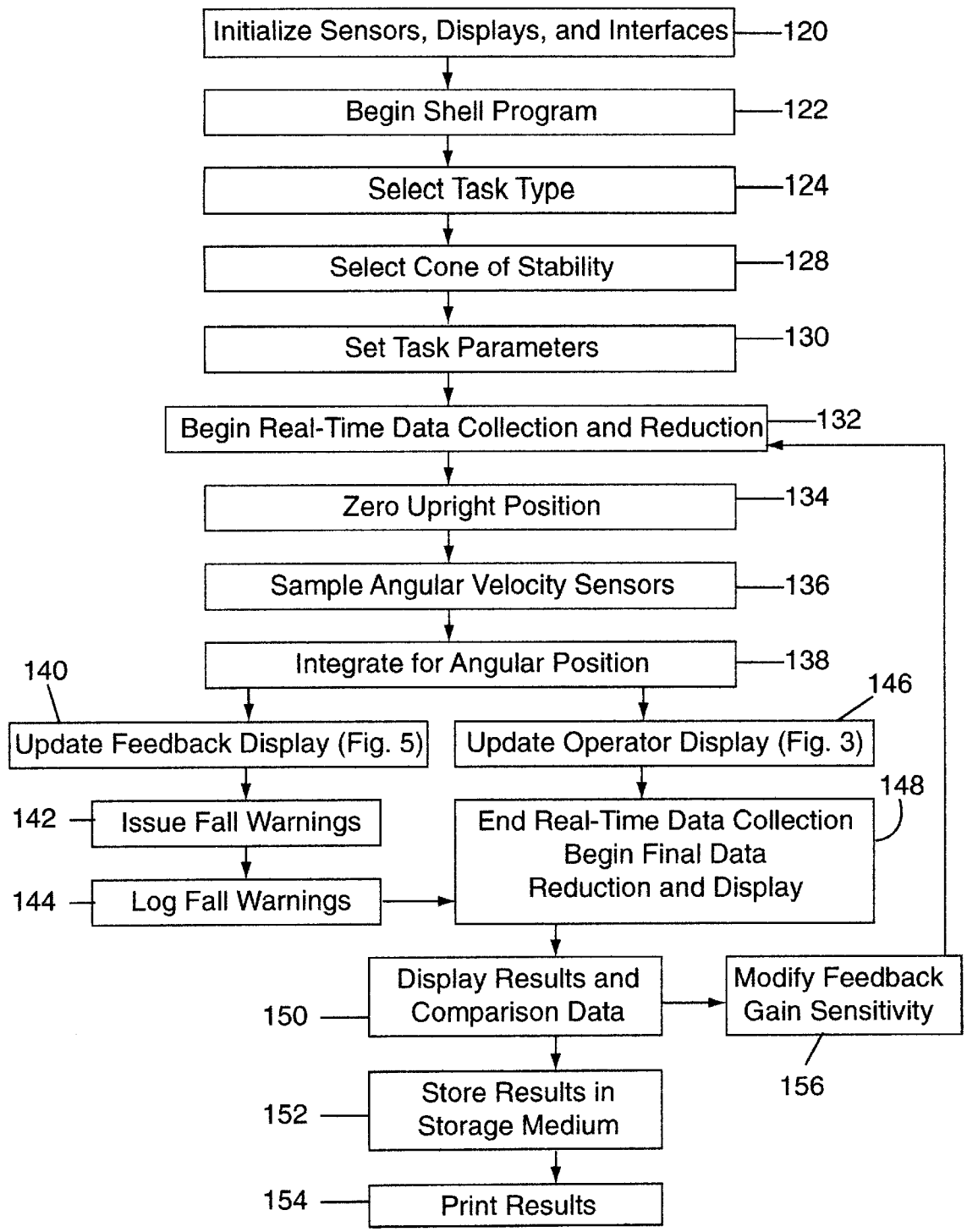
FIG. 6 is a flow chart illustrating the steps of an exemplary system processor control program algorithm for sampling body sway sensors, providing an operator's display, and providing visual body sway angle and angular velocity feedback in accordance with the present invention.

A flow chart illustrating an exemplary procedure that may be implemented by the system processor 14 to control the flow of information provided by the sensors 12, to generate the operator's display 40, to control a visual feedback system 24, and to allow an operator to intervene in the flow of information using an operator's input device 22, is described with reference to FIG. 6. It should be apparent that the steps of this procedure may be implemented as a computer program for controlling operation of the system processor 14 using conventional programming techniques. The first step 120 that the processor 14 completes prior to enabling operator control is to initialize and verify communication between the processor 14 and the body sway sensors 12, the operator's display unit 18, the feedback systems, e.g., the visual feedback system 24, and any other interfaces. An integral part of the initialization process will preferably include the periodic performance of a calibration procedure which is used to measure the bias of the body sway sensors 12 when no movement of the sensors is present other than that due to the earth's rotation. At step 122, a shell program is entered into. The shell program is used to define how real time data acquisition and output stages of the control procedure will operate. The shell program allows an operator to use the operator's input device 22 to enter subject data, e.g., name, date of birth, and medical history. At step 124, the operator is able to select the task type which the subject is to perform during the examination trial. At step 128, the operator is able to select the cone of stability that is to be used for analysis, to be displayed in the operator display 40, and to generate feedback warnings to a subject. The cone of stability to be used may be a cone of stability which has been defined for the particular subject and/or task, or both, or an average cone of stability derived from a particular sample population. Task parameters, e.g., duration of data recording, display scaling, and feedback gain sensitivities, are set at step 130 and are passed to the real time module for data collection and reduction which begins at step 132. Data collection begins by asking the operator to define the upright reference position for the subject at step 134. The upright reference position may preferably be selected as either true vertical, or a mean established by having the subject stand in his preferred vertical position for ten seconds. Thereafter, the body sway sensors 12 are sampled 136 at a preferred rate of, e.g., 50 samples per second. Assuming that the body sway sensors 12 are angular velocity transducers that provide signals indicative of the body sway angular velocity, an integration of the sensor signal values is performed at step 138 to yield body sway angular position values.

As has been described, the present invention may provide body sway angle and angular velocity feedback to the subject to improve the subject's gait and balance control. For a visual feedback system 24, this includes updating the visual feedback system display 90, which is performed at step 140. At step 142, a fall warning is provided when the subject's trunk sway is within one degree of the cone of stability. Fall warnings may be issued both to the subject, through the particular feedback system employed, as well as to the system operator. At step 144, any fall warnings issued at step 142 are logged for later retrieval by the operator. Simultaneously with updating of the visual feedback display 90, the operator's display 40 is updated at step 146. It should be apparent that steps 136–146 are repeated continuously throughout the examination trial period. On completion of the data acquisition phase, at step 148, the data gathered during the examination trial period is analyzed, reduced, and redisplayed to the operator in the operator's display 40. At step 150, previously stored body sway data may be retrieved from the system memory 16 for comparison with the information obtained during the examination trial period. Such previously stored information may include information gathered from normal or other sample populations for the particular task performed during the examination trial, or may be the particular subject's previous trial results with the current task. At step 152, the data from the current examination trial is stored in the processor system's memory 16. The operator may choose to print these results on the printer or plotter 20, at step 154. Based on the operator's examination of the examination trial results at step 150, the operator may change the sensitivities of the feedback gains at step 156, with the aim of further reducing the subject's trunk sway for the current task. The examination trial may then be repeated, by beginning real-time data collection once again, at step 132.

It should be apparent that control procedures other than the one described herein for exemplary purposes may be employed in accordance with the present invention. The order of procedural steps may be changed, steps may be added, and others may be deleted. Additionally, some of these procedural steps may occur simultaneously on separate system processors. For example, the step 140 of updating the visual feedback display 90 may be implemented on a portable processor attached to the subject, whereas the step 146 of updating the operator's display 40 may be implemented to occur simultaneously at a "remote" processor physically removed from the subject.

It should be understood that this invention is not confined or limited to the particular embodiments, implementations, and applications herein illustrated and described, but enhances all such modified forms thereof as come with in the scope of the following claims.

What is claimed is:

1. A body sway monitoring system, comprising:
   (a) a body sway sensor adapted to be attached to the body of a subject and providing continuous body sway signals indicative of the sway of the body;
   (b) a system processor means for deriving continuous body sway information from the body sway signals and for generating an operator display of the body sway information; and
   (c) an operator display means for displaying the operator display to an operator of the system.

2. The body sway monitoring system of claim 1 wherein the body sway sensor is adapted to be attached to the torso of the subject's body.

3. The body sway monitoring system of claim 1 including a body sway sensor adapted to be attached to the body of the subject to provide body sway signals indicative of the sway of the body in a pitch direction and a body sway sensor adapted to be attached to the body of the subject to provide body sway signals indicative of the sway of the body in a roll direction.

4. The body sway monitoring system of claim 1 wherein the body sway sensor includes an angular velocity transducer providing body sway signals indicative of the angular velocity of the body.

5. The body sway monitoring system of claim 1 wherein the body sway sensor includes acceleration transducers providing body sway signals indicative of the angular acceleration of the body.

6. The body sway monitoring system of claim 1 wherein the body sway sensor includes a position transducer providing body sway signals indicative of the angular displacement of the body.

7. The body sway monitoring system of claim 1 wherein the system processor means includes means for deriving body sway angle and body sway angular velocity information from the body sway signals and means for generating an operator display of the body sway angle and body sway angular velocity information.

8. The body sway monitoring system of claim 7 wherein the system processor means includes means for generating an operator display including a time history of the subject's body sway angle and body sway angular velocity over a trial period.

9. The body sway monitoring system of claim 1 wherein the system processor means further includes means for comparing the body sway information with a set of safety rules defining a cone of stability of the subject to obtain a measure of the subject's balance control and for incorporating the measure of the subject's balance control in the operator display.

10. The body sway monitoring system of claim 1 wherein the system processor means includes means for generating body sway feedback from the body sway information and further including a subject body sway feedback means for providing the body sway feedback to the subject.

11. The body sway monitoring system of claim 10 wherein the subject body sway feedback means includes means for providing the body sway feedback to the subject visually.

12. The body sway monitoring system of claim 11 wherein the means for providing the body sway feedback visually includes a head mountable subject display means for displaying a subject feedback display to the subject.

13. The body sway monitoring system of claim 10 wherein the subject body sway feedback means includes means for providing the body sway feedback to the subject aurally.

14. The body sway monitoring system of claim 10 wherein the subject body sway feedback means includes means for providing the body sway feedback to the subject through tactile stimulation of the subject's body.

15. The body sway monitoring system of claim 10 wherein the subject body sway feedback means includes means for providing the body sway feedback to the subject through electrical stimulation of the subject's vestibular nerve.

16. The body sway monitoring system of claim 10 wherein the system processor means includes means for comparing the body sway information with a set of safety rules defining an angular cone of stability of the subject and for incorporating a fall warning indication into the body sway feedback when the subject's body sway exceeds an angle greater than a selected fraction of the angular cone of stability, and wherein the subject body sway feedback means includes means for providing the fall warning indication to the subject.

17. A system for providing augmenting prosthetic body sway feedback to improve a subject's balance and movement control, comprising:
    (a) a body sway sensor adapted to be attached to the body of a subject and providing continuous body sway signals indicative of the sway of the body;
    (b) a system processor means for deriving continuous body sway information from the body sway signals and for generating body sway feedback from the body sway information; and
    (c) a subject body sway feedback means for providing the body sway feedback to the subject.

18. The system of claim 17 wherein the body sway sensor is adapted to be attached to the torso of the subject's body.

19. The system of claim 17 including a body sway sensor adapted to be attached to the body of the subject to provide body sway signals indicative of the sway of the body in a pitch direction and a body sway sensor adapted to be attached to the body of the subject to provide body sway signals indicative of the sway of the body in a roll direction.

20. The system of claim 17 wherein the body sway sensor includes an angular velocity transducer providing body sway signals indicative of the angular velocity of the body.

21. The system of claim 17 wherein the body sway sensor includes acceleration transducers providing body sway signals indicative of the angular acceleration of the body.

22. The system of claim 17 wherein the body sway sensor includes a position transducer providing body sway signals indicative of the angular displacement of the body.

23. The system of claim 17 wherein the system processor means includes means for deriving body sway angle and body sway angular velocity information from the body sway signals and means for generating the body sway feedback from the body sway angle and body sway angular velocity information.

24. The system of claim 17 wherein the subject body sway feedback means includes means for providing the body sway feedback to the subject visually.

25. The system of claim 24 wherein the means for providing the body sway feedback visually includes a head mountable subject display means for displaying a subject feedback display to the subject.

26. The system of claim 24 wherein the system processor means includes means for generating a subject feedback display including a central frame display and a bar that divides the central frame display into top and bottom fields and wherein the bar moves upward and downward in the central frame display when the subject's body sways forward and backward and wherein an angle of the bar in the central frame display is varied in response to left and right sway of the subject's body.

27. The system of claim 17 wherein the subject body sway feedback means includes means for providing the body sway feedback to the subject aurally.

28. The system of claim 17 wherein the subject body sway feedback means includes means for providing the body sway feedback to the subject both visually and aurally.

29. The system of claim 17 wherein the subject body sway feedback means includes means for providing the body sway feedback to the subject through tactile stimulation of the subject's body.

30. The system of claim 17 wherein the subject body sway feedback means includes means for providing the body sway feedback to the subject through electrical stimulation of the subject's vestibular nerve.

31. The system of claim 17 wherein the body sway feedback is related to the body sway information by feedback gain parameters, and comprising additionally means for adjusting the feedback gain parameters.

32. The system of claim 17 wherein the system processor means includes means for comparing the body sway information with a set of safety rules defining an angular cone of stability of the subject and for incorporating a fall warning indication into the body sway feedback when the subject's body sway exceeds an angle greater than a selected fraction of the angular cone of stability, and wherein the subject body sway feedback means includes means for providing the fall warning indication to the subject.

33. A central monitoring system for monitoring the body sway of one or more subjects, comprising:
    (a) a body sway sensor adapted to be attached to the body of each subject, each body sway sensor providing continuous body sway signals indicative of the sway of the subject's body;
    (b) a system processor means for deriving continuous body sway information for each subject from the body sway signals, for comparing the body sway information for each subject with a set of safety rules defining an angular cone of stability of the subject, and for generating a fall warning indication when a subject's body sway exceeds an angle greater than a selected fraction of the angular cone of stability; and (c) an operator display means for displaying the fall warning indication to an operator of the system.

34. The central monitoring system of claim 33 wherein the system processor means includes means for deriving body sway angle and body sway angular velocity information for each subject from the body sway signals and for generating an operator display of the body sway angle and body sway angular velocity information for each subject, and wherein the operator display means includes means for displaying the operator display.

35. The central monitoring system of claim 33 wherein the system processor means includes means for generating body sway feedback for each subject from the body sway information for each subject and further including a subject body sway feedback means for each subject for providing the body sway feedback to the subject.

36. The central monitoring system of claim 35 wherein the system processor means includes means for incorporating the fall warning indication into the body sway feedback, and wherein the subject body sway feedback means includes means for providing the fall warning indication to the subject.

37. The central monitoring system of claim 33 wherein the system processor means is remotely located from the subjects and further comprising wireless transmission means for transmitting the body sway signals from the body sway sensors to the system processor means.

38. A method for monitoring the body sway of a subject, comprising the steps of:

(a) attaching a body sway sensor to the body of a subject, the body sway sensor providing continuous body sway signals indicative of the sway of the body;

(b) deriving continuous body sway angle and body sway angular velocity information from the body sway signals and generating an operator display of the body sway angle and body sway angular velocity information; and (c) displaying the operator display to an operator of the system.

39. The method of claim 38 wherein the body sway sensor is attached to the torso of the subject's body.

40. The method of claim 38 wherein the step of attaching a body sway sensor to the body of a subject includes the steps of attaching a first body sway sensor to the body of the subject to provide body sway signals indicative of the sway of the body in a pitch direction and attaching a second body sway sensor to the body of the subject to provide body sway signals indicative of the sway of the body in a roll direction.

41. The method of claim 38 wherein the body sway sensor includes an angular velocity transducer providing body sway signals indicative of the angular velocity of the body.

42. The method of claim 38 wherein the body sway sensor includes acceleration transducers providing body sway signals indicative of the angular acceleration of the body.

43. The method of claim 38 wherein the body sway sensor includes a position transducer providing body sway signals indicative of the angular displacement of the body.

44. The method of claim 38 wherein the step of generating an operator display includes the step of generating a time history of the subject's body sway angle and body sway angular velocity over a trial period.

45. The method of claim 38 comprising additionally the steps of comparing the body sway angle information with a set of safety rules defining a cone of stability of the subject to obtain a measure of the subject's balance control and for incorporating the measure of the subject's balance control in the operator display.

46. The method of claim 38 comprising additionally the step of comparing the body sway angle and angular velocity information to normal body sway information.

47. The method of claim 38 comprising additionally the step of comparing the body sway angle and angular velocity information to body sway information of the subject obtained during past performance of a particular task.

48. The method of claim 38 comprising the additional steps of generating body sway feedback from the body sway angle and angular velocity information and providing the body sway feedback to the subject.

49. The method of claim 48 wherein the step of providing the body sway feedback to the subject includes the step of providing the body sway feedback to the subject visually.

50. The method of claim 48 wherein the step of providing the body sway feedback to the subject includes the step of providing the body sway feedback to the subject aurally.

51. The method of claim 48 wherein the step of providing the body sway feedback to the subject includes the step of providing the body sway feedback to the subject through tactile stimulation of the subject's body.

52. The method of claim 48 wherein the step of providing the body sway feedback to the subject includes the step of providing the body sway feedback to the subject through electrical stimulation of the subject's vestibular nerve.

53. The method of claim 48 comprising additionally the steps of comparing the body sway angle information with a set of safety rules defining an angular cone of stability of the subject, generating a fall warning indication when the subject's body sway exceeds an angle greater than a selected fraction of the angular cone of stability, and providing the fall warning indication to the subject.

54. A method for providing augmenting prosthetic body sway feedback to improve a subject's balance and movement control, comprising the steps of:

(a) attaching a body sway sensor to the body of a subject, the body sway sensor providing continuous body sway signals indicative of the sway of the body;

(b) deriving continuous body sway angle and body sway angular velocity information from the body sway signals and generating body sway feedback from the body sway angle and angular velocity information; and (c) providing the body sway feedback to the subject.

55. The method of claim 54 wherein the step of attaching a body sway sensor to the body of a subject includes the step of attaching a body sway sensor to the torso of the subject's body.

56. The method of claim 54 wherein the step of attaching a body sway sensor to the body of a subject includes the steps of attaching a first body sway sensor to the body of the subject to provide body sway signals indicative of the sway of the body in a pitch direction and attaching a second body sway sensor to the body of the subject to provide body sway signals indicative of the sway of the body in a roll direction.

57. The method of claim 54 wherein the body sway sensor includes an angular velocity transducer providing body sway signals indicative of the angular velocity of the body.

58. The method of claim 54 wherein the body sway sensor includes acceleration transducers providing body sway signals indicative of the angular acceleration of the body.

59. The method of claim 54 wherein the body sway sensor includes a position transducer providing body sway signals indicative of the angular displacement of the body.

60. The method of claim 54 wherein the step of providing the body sway feedback to the subject includes the step of providing the body sway feedback to the subject visually.

61. The method of claim 54 wherein the step of providing the body sway feedback to the subject includes the step of providing the body sway feedback to the subject aurally.

62. The method of claim 54 wherein the step of providing the body sway feedback to the subject includes the step of providing the body sway feedback to the subject through tactile stimulation of the subject's body.

63. The method of claim 54 wherein the step of providing the body sway feedback to the subject includes the step of providing the body sway feedback to the subject through electrical stimulation of the subject's vestibular nerve.

64. The method of claim 54 comprising additionally the steps of comparing the body sway information with a set of safety rules defining an angular cone of stability of the subject, generating a fall warning indication when the subject's body sway exceeds an angle greater than a selected fraction of the angular cone of stability, and providing the fall warning indication to the subject.

65. A method for monitoring the body sway of one or more subjects, comprising the steps of:

(a) attaching a body sway sensor to the body of each subject, each body sway sensor providing continuous body sway signals indicative of the sway of the subject's body;

(b) deriving continuous body sway information for each subject from the body sway signals, comparing the body sway information for each subject with a set of safety rules defining an angular cone of stability of the subject, and generating a fall warning indication when a subject's body sway exceeds an angle greater than a selected fraction to the angular cone of stability; and (c) displaying the fall warning indication to an operator of the system.

66. The method of claim 65 comprising additionally the steps of generating body sway feedback for each subject from the body sway information for each subject and providing the body sway feedback to the subject.

67. The method of claim 65 comprising additionally the step of providing the fall warning indication to the subject.

* * * * *

UNITED STATES PATENT AND TRADEMARK OFFICE
CERTIFICATE OF CORRECTION

PATENT NO. : 5,919,149
DATED : July 6, 1999
INVENTOR(S) : John H. Allum

It is certified that error appears in the above-indentified patent and that said Letters Patent is hereby corrected as shown below:

Add to the first page of the patent:

Foreign Application Priority Data

Mar. 19, 1996 [EP] European Patent Office           96104356.9

Signed and Sealed this

Twenty-fifth Day of July, 2000

Attest:

Q. TODD DICKINSON

*Attesting Officer*          *Director of Patents and Trademarks*